United States Patent
Hamilton et al.

(10) Patent No.: US 6,462,072 B1
(45) Date of Patent: Oct. 8, 2002

(54) CYCLIC ESTER OR AMIDE DERIVATIVES

(75) Inventors: Gregory S. Hamilton, Catonsville; David C. Limburg, Baltimore, both of MD (US)

(73) Assignee: GPI NIL Holdings, Inc., Wilmington, DE (US)

( * ) Notice: Subject to any disclaimer, the term of this patent is extended or adjusted under 35 U.S.C. 154(b) by 0 days.

(21) Appl. No.: 09/157,566

(22) Filed: Sep. 21, 1998

(51) Int. Cl.[7] ..................... A61K 31/401; C07D 207/16
(52) U.S. Cl. ................. 514/423; 548/533; 548/537
(58) Field of Search .................. 548/533, 537; 514/423

(56) References Cited

U.S. PATENT DOCUMENTS

| | | | |
|---|---|---|---|
| 4,070,361 A | 1/1978 | Petrillo, Jr. | 260/293.85 |
| 4,206,137 A | 6/1980 | Condon et al. | 260/455 |
| 4,310,461 A | 1/1982 | Krapcho et al. | 260/326.2 |
| 4,374,829 A | 2/1983 | Harris et al. | 424/177 |
| 4,390,695 A | 6/1983 | Krapcho et al. | 544/130 |
| 4,531,964 A | 7/1985 | Shimano et al. | 71/92 |
| 4,574,079 A | 3/1986 | Gavras et al. | 424/1.1 |
| 4,578,474 A | 3/1986 | Krapcho et al. | 546/188 |
| 4,593,102 A | 6/1986 | Shanklin, Jr. | 546/216 |
| 4,808,573 A | 2/1989 | Gold et al. | 514/19 |
| 4,818,749 A | 4/1989 | Gold et al. | 514/19 |
| 5,147,877 A | 9/1992 | Goulet | 514/291 |
| 5,192,773 A * | 3/1993 | Armistead et al. | 514/315 |
| 5,252,579 A | 10/1993 | Skotnicki et al. | 514/291 |
| 5,294,603 A | 3/1994 | Rinehart | 514/10 |
| 5,319,098 A | 6/1994 | Burbaum et al. | 548/533 |
| 5,516,797 A | 5/1996 | Armistead et al. | 514/548 |
| 5,543,423 A | 8/1996 | Zelle et al. | 514/332 |
| 5,614,547 A | 3/1997 | Hamilton et al. | 514/423 |
| 5,631,017 A | 5/1997 | Sharpe et al. | 424/449 |
| 5,686,424 A * | 11/1997 | Connell et al. | 514/19 |
| 5,696,135 A | 12/1997 | Steiner et al. | 514/317 |
| 5,703,088 A | 12/1997 | Sharpe et al. | 514/278 |
| 5,721,256 A | 2/1998 | Hamilton et al. | 514/330 |
| 5,786,378 A | 7/1998 | Hamilton et al. | 514/423 |
| 5,795,908 A | 8/1998 | Hamilton et al. | 514/423 |
| 5,798,355 A | 8/1998 | Steiner et al. | 514/248 |
| 5,801,187 A | 9/1998 | Li et al. | 514/365 |
| 5,801,197 A | 9/1998 | Steiner et al. | 514/548 |

FOREIGN PATENT DOCUMENTS

| | | |
|---|---|---|
| DE | 3508251 | 9/1986 |
| DE | 3931051 | 3/1990 |
| DE | 4015255 | 11/1991 |
| EP | 12401 | 6/1980 |
| EP | 48159 | 3/1982 |
| EP | 50800 | 5/1982 |
| EP | 73143 | 3/1983 |
| EP | 88350 | 9/1983 |
| EP | 196841 | 10/1986 |
| EP | 260118 | 3/1988 |
| EP | 333174 | 9/1989 |
| EP | 352000 | 1/1990 |
| EP | 378318 | 7/1990 |
| EP | 405994 | 1/1991 |
| EP | 419049 | 3/1991 |
| EP | 468339 | 1/1992 |
| EP | 572365 | 12/1993 |
| EP | 652229 | 5/1995 |
| GB | 2247456 | 3/1992 |
| JP | 55160757 | 12/1980 |
| JP | 04149166 | 5/1992 |
| JP | 05178824 | 7/1993 |

(List continued on next page.)

OTHER PUBLICATIONS

Ando, Takao et al., "Formation of Crossed Phenzine from the Reaction between Tetra–p–anisyl– and Tetra–p–tolyl–hydrazines in Liquid Sulphur Dioxide," Chem. Comm., S. Chem. Comm., 1975, 989.

Andrus, Merrit B., "Structure–based design of an acyclic ligand that bridges FKBP12 and calcineurin," J. Am. Chem. Soc., 1993, 115(2), 10420–1.

Armistead, D.M. et al., "Design, synthesis and structure of non–macrocyclic inhibitors of FKBP12, the major binding protin for the immunosuppressant FK506," Acta Crystallogr. 1995, D51(4), 522–8.

Askin, D. et al., "Chemistry of FK–506: benzilic acid rearrangement of the tricarbonyl system," Tetrahedron Lett., 1989, 30(6), 671–4.

Askin, D. et al., "Effecient Degradation of FK–506 to a versatile synthetic intermediate," J. Org. Chem., 1990, 55(20), 5451–4.

Baader, Ekkehard et al., "Inhibition of prolyl 4–hydroxylase by oxalyl amino acid derivatives in vitro, in isolated microsomes and in embryonic chicken tissues," Biochem. J., 1994, 300(2), 525–30.

Baumann, K. et al., "Synthesis and oxidative cleavage of the major equilibrium products of ascomycin and Fk 506," Tetrahedron Lett., 1995, 26(13), 2231–4.

Bender, D., et al., "Periodate oxidation of α–keto γ–lactams. Enol oxidation and β–lactam formation. Mechanism of periodate hydroxylation reactions," J. Org. Chem., 1978, 43(17), 3354–62.

Birkenshaw, T.N. et al., "Synthetic FKBP12 Ligands. Design and Synthesis of Pyranose Replacements," *Bioorganic & Medicinal Chemistry Letters*, (1994) 4:21, 2501–2506.

Boulmedais, Ali et al., "Stereochemistry of Electrochemical Reduction of Optically Active α–ketoamides. II. Electroreduction of benzoylformamides derived from S–(–)–proline," Bull. Soc. Chim. Fr., 1989, (2), 185–91. (French).

(List continued on next page.)

Primary Examiner—Richard L. Raymond
Assistant Examiner—Hong Liu
(74) Attorney, Agent, or Firm—Lyon & Lyon LLP

(57) ABSTRACT

This invention relates to low molecular weight, small molecule cyclic esters and amides having an affinity for FKBP-type immunophilins, pharmaceutical compositions comprising the same, and methods of using the same to effect a neuronal activity.

22 Claims, No Drawings

FOREIGN PATENT DOCUMENTS

| | | |
|---|---|---|
| WO | WO8809789 | 12/1988 |
| WO | WO9012805 | 11/1990 |
| WO | WO9104985 | 4/1991 |
| WO | WO9113088 | 9/1991 |
| WO | WO9200278 | 1/1992 |
| WO | WO9203472 | 3/1992 |
| WO | WO9204370 | 3/1992 |
| WO | WO9216501 | 10/1992 |
| WO | WO9218478 | 10/1992 |
| WO | WO9219593 | 11/1992 |
| WO | WO9219745 | 11/1992 |
| WO | WO9221313 | 12/1992 |
| WO | WO9307269 | 4/1993 |
| WO | WO9313066 | 7/1993 |
| WO | WO9323548 | 11/1993 |
| WO | WO9325546 | 12/1993 |
| WO | WO9405639 | 3/1994 |
| WO | WO9407858 | 4/1994 |
| WO | WO9413629 | 6/1994 |
| WO | WO9512572 | 5/1995 |
| WO | WO9524385 | 9/1995 |
| WO | WO9526337 | 10/1995 |
| WO | WO9535308 | 12/1995 |
| WO | WO9535367 | 12/1995 |
| WO | WO9606097 | 2/1996 |
| WO | WO9615101 | 5/1996 |
| WO | WO9617816 | 6/1996 |
| WO | WO9603318 | 10/1996 |
| WO | WO9633184 | 10/1996 |
| WO | WO9633187 | 10/1996 |
| WO | WO9636630 | 11/1996 |
| WO | WO 96 41609 | 12/1996 |
| WO | WO 98 13355 | 5/1998 |
| WO | WO9820891 | 5/1998 |
| WO | WO9820892 | 5/1998 |
| WO | WO9820893 | 5/1998 |
| WO | WO9824805 | 6/1998 |
| WO | WO 98 55090 | 12/1998 |
| WO | WO 9929695 | 6/1999 |
| ZA | 9207782 | 4/1993 |

OTHER PUBLICATIONS

Cameron, Andrew et al., "Immunophilin FK506 binding protein associated with inositol 1,4,5–triphosphate receptor modulates calcium flux," Proc. Natl. Acad. Sci. USA, 1995, 92, 1784–1788.

Caufield, Craig E. and Musser, John H., "Macrocyclic Immunomodulators," *Annual Reports in Medicinal Chemistry,* Johns (Ed.), Academic Press, Chapter 21, 195–204, 1989.

Caffrey, M.V. et al., "Synthesis and Evaluation of Dual Domain Macrocyclic FKBP12 Ligands," *Bioorganic & Medicinal Chemistry Letters,* (1994) 4:21, 2507–2510.

Chakraborty, TK et al., "Design and Synthesis of a rampamycin–based high affinity binding FKBP12 ligand," Chem. Biol., 1995, 2(3), 157–61.

Chakaraborty, Tushar K., "Studies towards the development of cyclic peptide–based analogs of macrolide immunosuppressants," Pure Appl. Chem., 1996, 68(3), 565–568.

Coleman, R., and Danishefsky, S., "Degradation and manipulations of the immunsuppressant FK506: preparation of potential synthetic intermediates" Heterocycles, 1989, 28(1), 157–61.

Colombo, L. et al., "Enantioselective synthesis of secondary alcohols in the presence of chiral ligands," Tetrahedron, 1982, 38(17), 2725–7.

Cunliffe, C. Jane et al., "Novel inhibitors of prolyl 4–hydroxylase. 3. Inhibition by the substrate analog N–oxaloglycine and its derivatives," J. Med. Chem., 1992, 35 (14), 2652–8.

Cushman, D.W. et al., "Design of potent competitive inhibitors of angiotensin–converting enzyme. Carboxyalkanoly and mercaptoalkanoyl amino acids," Biochemistry, 1977, 16(25), 5484–91.

Dawson, Ted M. et al., "Immunosuppressant FK506 enhances phosphorylation of nitric oxide synthase and protects against glutamate neurotoxicity," Proc. Natl. Acad. Sci. USA, 1993, 90, 9808–12.

Dawson, T.M. et al., "The immunophilins, FK506 binding and cyclophilin, are discretely localized in the brain: relationship to calcineurin," Neuroscience, 1994, 62(2), 569–80.

Effenberger F. et al., "Diastereoselective addition of benzenesulfenyl chloride to 1–acryloylproline esters," Chemical Abstracts, 1989, 110:154846h.

Egbertson, M. and Danishefsky, S., "A synthetic route to the tricarbonyl region of FK–506," J. Org. Chem., 1989, 54(1), 11–12.

Feutren, Gilles, "The Optimal use of Cyclosporin A in Autoimmune Diseases," J. of Autoimmunity, 1992, 5, 183–95.

Finberg, Robert W. et al., "Prevention of HIV–1 Infection and Preservation of CD4 Function by the binding of CPFs to gp120," Science, 1990, 249, 287–91.

Fisher, Matthew et al., "On the remarkable propensity for carbon–carbon bond cleavage reactions in teh C(8)–C(10) region of FK–506," J. Org. Chem., 1991, 56(8), 2900–7.

Fry, Lionel, "Psoriasis: Immunopathology and Long–term treatment with Cyclosporin," J. of Autoimmunity, 1992, 5, 277–83.

Furber, Mark, "FKBP–12–ligand–calceineurin interactions: analogs of SBL506," J. Am. Chem. Soc., 1995, 117(27), 7267–8.

Furber, M. et al., "Studies relating to the immunosuppressive activitiy of FK506," Tetrahedron Lett., 1993, 34(8), 1351–4.

Goodfellow, Val S. et al., "p–Nitrophenyl 3–diazopyruvate and diazopyruvamides, a New Family of Photoactivatable Cross–Linking Bioprobes," Biochemistry, 28(15), 6346–60.

Goulet, Mark T., and Boger, Joshua, "Degradative studies on the tricarbonyl containing macrolide rapamycin," Tetrahedron Lett., 1990, 31(34), 4845–8.

Goulet, Mark T. and Boger, Joshua, "Degradative studies on the tricarbonyl containing macrolide rapamycin," Tetrahedron Lett., 1991, 32(45), 6454.

Haeusler, Johannes and Schmidt, Ulrich, "Amino acids and peptides. IX. Pyruv oyl amino acids," Chem. Ber., 1974, 107(1), 145–51. (German).

Harding, M.W., et al., "A receptor for the immunosuppressant FK506 is a cis–trans peptidyl–prolyl isomerase," Nature Lett., 1989, 341, 758–60.

Hauske, J.R. et al. "Design and Synthesis of Novel FKBP Inhibitors," *J. of Medicinal Chemistry,* (1992) 35, 4284–4296.

Hauske, James R. et al., "Investigation of the effects of synthetic, non–cytotoxic immunophilin inhibitors on MDR," Bioorg. Med. Chem.. Lett., 1994, 4(17), 2097–102.

Hayward, C.M. et al., "Total Synthesis of rapamycin via a novel titanium–mediated aldol macrocyclization reaction," J. Am. Chem. Soc., 1993, 115(20), 9345–6.

Hayward, C.M. et al., "An application of the Suarez reaction to the regiospecific synthesis of the $C_{28}$–$C_{42}$ segment of rapamycin," 3989–92.

Holt, D.A. et al., "Design, Synthesis, and Kinetic Evaluation of High–Affinity FKBP Ligands and the X–ray Crystal Structures of Their Complexes with FKBP12," *J. Am. Chem. Soc.,* (1993) 115, 9925–9938.

Holt, D.A. et al., "Structure–Activity Studies of Nonmacrocyclic Rapamycin Derivatives," *Bioorganic & Medicinal Chemistry Letters,* (1993) 3:10, 1977–1980.

Holt, D.A. et al., "Structure–Activity Studies of Synthetic FKBP Ligands as Peptidyl–prolyl Isomers Inhibitors," *Bioorganic & Medicinal Chemistry Letters,* (1994) 4:2, 315–320.

Hearn, Walter R., and Worthington, Robert E., "L–Proline–N–oxalic anhydride," J. Org. Chem., 1967, 32(12), 4072–4.

Iwabuchi, T. et al., "Effects of immunosuppressive peptidyl–prolyl cis–trans isomerase (PPIase inhibitors, cyclosporin A, FK506, ascomycin and rapamycin, on hair growth initiation in mouse: immunosuppression is not required for hair growth," *J. of Deramatol. Sci.,* (1995) 9:1, 64–69.

Jiang, H. et al., "Induction of anagen in telogen mouse skin by topical application of FK506, a potent immunosuppressant," *J. Ivest. Dermatol.,* (1995) 104:4, 523–525.

Jones, T. et al., "Chemistry of tricarbonyl hemiketals and application of Evans technology to the total synthesis of the immunosuppressant (−)–FK–506," J. Am. Chem. Soc., 1990, 112(8), 2998–3017.

Jones, A. et al., "A formal synthesis of FK–506. Exploration of some alternatives to macrolactamization," J. Org. Chem., 1990, 55(9), 2786–97.

Kaczmar, et al., Makromol. Chem., 1976, 177, 1981–9 (German).

Karle, Isabella L. et al., "Conformation of the oxalamide group in retro–bispeptides. Three crystal structures," Int. J. Pept. Protein Res., 1994, 43(2), 160–5.

Kino, Toru et al., "FK–506, A novel immunosuppressnt isolateded from A streptomyces," J. of Antibiotics, 1987, 40(9), 1249–55.

Kocienski, P. et al., "A synthesis of the C(1)–C(15) segment of tsukubaenolide (FK506)," Tetrahedron Lett., 1988, 29(35), 4481–4.

Krit, N.A. et al., "Impact of the nature of alkyl radical on the biological activity of N–carboxyalkyl dipeptides," Khim.–Farm. Zh., 1991, 25(7), 44–6. (Russian).

Linde, Robert G. et al., "Straightforward synthesis of 1,2,3–tricarbonyl systems," J. Org. Chem., 1991, 56(7), 2534–8.

Luengo, Juan I. et al., "Efficient removal of pipecolinate from rapamycin and FK506 by reaction with tetrabutylammonium cyanide," Tetrahedron Lett., 1993, 34(29), 4599–602.

Luengo, J. et al., "Structure–activity studies of rapamycin analogs: evidence that the C–7 methodoxy group is part of the effector domain and positioned at the FKBP:12–FRAP interface," Chem. Biol., 1995, 2(7), 471–81.

Lyons, W. Ernest et al., "Neronal regeneration Enhances the Expression of the Immunophilin FKBP–12," The Journal of Neuroscience, 1995, 15, 2985–94.

Marshall, J.A. et al., Convenient synthesis of dioxopiperazines via aminolysis of .alpha.–(pyruvylamino) esters, Synth. Commun., 1975, 5(3), 237–44.

Mashkovskii, M.D. et al., "1–[4–(2–Hydroxy–3–tert–butylaminopropoxy)–indole–3–yl (5–acetamido–1–(S)–carboxypentyl)–DL–alanyl]–L–proline dihydrochloride, a new angiotensin–converting enzyme inhibitor with β–adrenoblocking properties," Khim.–Farm. Zh., 1993, 27(10), 16–20. (Russian).

Munegumi, Toratane et al., "Asymmetric Catalytic Hydrogenations of N–pyruvoyl–(S)–proline esters," Bull. Chem. Soc. Jpn., 1987, 60(1), 243–53.

Munoz, Benito et al., "α–Ketoamide Phe–Pro isostere as a new core structure for the inhibition of HIV protease," Bioorg. Med. Chem., 1994, 2(10), 1085–90.

Nakatsuka, M et al. "Total Synthesis of FK506 and an FKBP Reagent, ($C_8$, $C_9$–$^{13}C_2$)–FK–506," J. Am. Chem. Soc., 1990, 112 (14), 5583–90..

Nelson, F. et al., "A novel ring contraction of rapamycin," Tetrahedron Lett., 1994, 35(41), 7557–60.

Nicolaou, K.C. et al., "Total Synthesis of rapamycin," J. Am. Chem. Soc., 1993, 115(10), 4419–20.

Pattenden, Gerald and Tankard, Mark, "Facile Synthesis of the tricarbonyl subunit in the immunosuppressant rapamycin," Tetrahedron Lett., 1993, 34(16), 2677–80.

Ponticelli, Claudio, "Treatment of the Nephrotic Syndrome with Cyclosporin A," J. of Autoimmunity, 1992, 5, 315–24.

Ranganathan, Darshan et al., "Protein Backbone Modification by Novel Cα–C Side–Chain Scission," 1994, J. Am. Chem. Soc., 116(15), 6545–57.

Rao, A.V., et al., "Studies directed towards the synthesis of immunosuppressive agent FK–506: construction of the tricarbonyl moiety," Tetrahedron Lett., 1990, 31(10), 1439–42.

Rao, A.V. Rama et al., "Studies directed towards the synthesis of immunosuppressive agent FK–506: synthesis of the entire bottom half," Tetrahedron Lett., 1991, 32(9), 1251–4.

Rao, A.V. Rama and Desibhatla, Vidyanand, "Studies directed towards the syntesis of rapamycin: stereoselective synthesis of C–1 to C–15 segment,"Tetrahedron Lett., 1993, 34(44), 7111–14.

Shu, A. et al., "Synthesis of I–125 labeled photoaffinity rapamycin analogs," J. Labelled Compd. Radiopharm., 1996, 38(3), 277–37.

Skotnicki, Jerauld et al., "Ring expanded rapamycin derivatives," Tetrahedron Lett., 1994, 35(2), 201–2.

Skotnicki, Jerauld et al., "Synthesis of secorapamycin esters and amides," Tetrah. Lett., 1994, 35(2), 197–200.

Slee, Deborah H. et al., Selectivity in the Inhibition of HIV and FIV Protease: Inhibitory and Mechanistic Studies of Pyrrolidine–Containing α–Keto Amide and Hydroxyethylamine Core Structures, J. Am. Chem. Soc., 1995, 117(48), 1187–78.

Smith, A.B. et al., "Total synthesis of rapamycin and demethoxyrapamycin," J. Am. Chem. Soc., 1995, 117 (19), 5407–8.

Soai, Kenso and Ishizaki, Miyuki, "Diastereoselective asymmetric allylation of chiral α–keto amides with allyltrimethylsilane. Preparation of protected homoallylic alcohols," J. Chem. Soc., 1984, 15, 1016–1017.

Soai, Kenso et al., "Asymmetric Allylation of α–keto amides Derived from (S)–proline esters," Pept. Chem., 1986, 24, 327–330.

Soai, Kenso and Ishizaki, Miyuki, "Asymmetric Synthesis of Functionalized tertiary alcohols by diastereoselective allylation of chiral α–keto amides derived from (S)–proline esters: control of stereochemistry based on saturated coordination of Lewis acid," J. Org. Chem., 1986, 57(17) 3290–5. (English).

Soai, Kenso et al., "Asymmetric synthesis of both eaniomers of α–hydroxy acids by the diastereoselective reduction of chiral α–keto amides with complex metal hydrides in the presence of a metal salt," Chem. Lett., 1986, 11, 1897–900.

Steffan, Robert J. et al., "Base catalyzed degradations of rapamycin," Tetrahedron Lett., 1993, 34(23), 3699–702.

Steglich, Wolfgang et al., "Activated carboxylic acid derivatives. II. A simple synthesis of 2–oxycarboxylic acid amides, N–(2–oxoacyl)amino acid esters and 2–oxocarboxylic acid hydrazides," Synthesis, 1978, 8, 622–4. (German).

Steiner, Joseph P. et al., "High brain densities of the immunophilin FKBP colocalized with calcineurin," Nature Lett., 1992, 358, 584–7.

Steiner, J.P. et al., "Nonimmunosuppressive Ligands for Neuroimmunophilins Promote Nerve Extension In Vitro and In Vivo," Society for Neuroscience Abstracts, 1996, 22, 297.13.

Stocks, M. et al., "The contribution to the binding of the pyranoside sustituents in the excised binding domain of FK–506," Bioorg. Med. Chem. Lett., 1994, 4(12), 1457–60.

Stocks, M. et al., "Macrocyclic ring closures employing the intramolecular Heck reaction," Tetrahedron Lett., 1995, 36(36), 6555–8.

Tanaka, H. et al., "Structure of FK506, a novel imunosuppressant isolated from Streptomyces," J. Am. Chem. Soc., 1987, 109(16), 5031–3.

Tatlock, J. et al., "High affinity FKBP–12 ligands from (R)–(–)–carvone. Synthesis and evaluation of FK506 pyranose ring replacements," Bioorg. Med. Chem. Lett., 1995, 5(21), 2489–94.

Teague, S.J. et al., "Synthesis and Study of a Non–Macrocyclic FK506 Derivative," Bioorg. Med. Chem. Lett., (1994) 4:13, 1581–1584.

Teague, S. et al., "Synthesis of FK506–cyclosporin hybrid macrocycles," Bioorg. Med. Chem. Lett., 1995, 5(20), 2341–6.

Tindall, Richard S.A., "Immunointervention with Cyclosporin A in utoimmune Neurological Disorders," J. of Autoimmunity, 1992, 5, 301–13.

Tugwell, Peter, "Cyclosporin in the Treatment of Rheumatoid Arthritis," J. of Autoimmunity, 1992, 5, 231–40.

Waldmann, Herbert, "Proline benzyl ester as chiral auxilary in Barbier–type reactions in aqueous solution," 1990, Synlett, 10, 627–8.

Wang, C.P. et al., "High performance liquid chromatographic isolation and spectroscopic characterization of three major metabolites from the plasma of rats receiving rapamycin (sirolimus) orally," J. Liq. Chromatogr., 1995, 18(13), 2559–68.

Wang, C.P. et al., "A high performance liquid chromatographic method for the determination of rapamycin {sirolimus} in rat serum, plasma, and blood and in monkey serum," J. Liq. Chromatogr., 1995, 18(9), 1801–8.

Wang, G.T. et al., Synthesis and FKBP Binding of Small Molecule Mimics of the Tricarbonyl Region of FK506, Bioorg. Med. Chem. Lett., (1994) 4:9, 1161–1166.

Wasserman, H.H. et al., "Synthesis of the tricarbonyl region of FK–506 through and amidophosphorane [Erratum to document cited in CA111(7):57366p]," J. Org. Chem., 1989, 54(22), 5406.

Whitesell, J.K. et al., "Asymmetric Induction. Reduction, Nucleophilic Addition to, Ene Reactions of Chiral α–Ketoesters," J. Chem. Soc., Chem Commun., 1983, 802.

Williams, D.R. and Benbow, J.W., "Synthesis of the α,β diketo amide segment of the novel immunosuppressive FK506," J. Org. Chem., 1988, 53(191), 4643–4.

Yohannes, Daniel et al., "Degradation of rapamycin: synthesis of a rapamycin–derived fragment containing the tricarbonyl and triene sectors," Tetrahedron Lett., 1993, 34(13), 2075–8.

Yamamoto, S. et al., "Stimulation of hair growth by topical application of DK506, a potent immunosuppressive agent," J. Invest. Dermatol, (1994) 102:2, 160–164.

Zaparucha et al., "Asymmetric Synthesis of 3–alkyl pipecolic acids", Tetrahedron Lett. vol. 40, No. 9, 1999 pp. 3699–3700. (CAS 1999:296090).

Asaoka et al., "Chelation controlled cis–selective acylation of 2–(alkoxycarbonyl)cyclopentylzinc iodides", J. Chem. Soc., Perkin Trans. 1 vol. 20, 1997 pp. 2949–2950. (CAS 1997:711908).

Serebryakov et al., "Synthesis of 3–formyl–2–caproyl–1–cyclopentanol from 2–cyclopentenone", Izv. Akad. Nauk SSSR, Ser. Khim vol. 8, 1978 pp. 1904–1906. (CAS 1978:597012).

Sugie et al., "Synthesis of carbocyclic analogs of captopril (SQ–14225)" Chem. Pharm. Bull. vol. 27, No. 9, 1979 pp. 1708–1709 (CAS 1980:41393).

Groves, John Kington, "Pyrrole chemistry. XV. Chemistry of some 3,4–disubstituted pyrroles" Can. J. Chem. vol. 51, No. 7 pp. 1089–1098. (CAS 1973:405203).

Chemical Abstracts Service Accession No. 1999:388188, Document No. 131:44836.

Chemical Abstracts Service Accession No. 1999:296090, Document No. 131:45075.

Chemical Abstracts Service Accession No. 1997:711908, Document No. 128:22643.

Chemical Abstracts Service Accession No. 1981:406626, Document No. 95:6626.

Chemical Abstracts Service Accession No. 1980:585834, Document No. 93:185834.

Chemical Abstracts Service Accession No. 1980:41393, Document No. 92:41393.

Chemical Abstracts Service Accession No. 1979:610910, Document No. 91:210910.

Chemical Abstracts Service Accession No. 1978:597012, Document No. 89:197102.

Chemical Abstracts Service Accession No. 1973:405203, Document No. 79:5203.

Printout for Konobevtsev et al. Stomatologiya, 61:7–9, 1982.*

Printout for Nishizawa et al., J. Antibiot, 41: 1629–43, 1988.*

Printout for Fukazawa et al. EP 333522, Sep. 1989.*

CAS Printout for Morita et al. JP 04009367, Jan. 1992.*

CAS Printout Holt et al. Bioorg Med. Chem. Lett., 4:315–20, 1994.*

CAS Printout for Steiner et al. Proc. Natl. Acad. Sci., 94 2019:2024, 1997.*

CAS Printout for Armistead et al. US 5654332, Aug. 1997.*

CAS Printout for Ognyanov et al. WO 9745115, Dec. 1997.*

CAS Printout for Armistead et al. US 5723459, Mar. 1998.*

CAS Printout for Lamb et al. J. Med. Chem., 41:3928–3939, 1998.*

* cited by examiner

CYCLIC ESTER OR AMIDE DERIVATIVES

BACKGROUND OF THE INVENTION

1. Field of Invention

This invention relates to neurotrophic low molecular weight, small molecule cyclic ester or amide derivatives having an affinity for FKBP-type immunophilins, pharmaceutical compositions comprising the same, and methods of using the same to effect a neuronal activity.

2. Description of Related Art

The term immunophilin refers to a number of proteins that serve as receptors for the principal immunosuppressant drugs, cyclosporin A (CsA), FK506, and rapamycin. Known classes of immunophilins are cyclophilins and FK506 binding proteins, or FKBPs. Cyclosporin A binds to cyclophilin A, while FK506 and rapamycin bind to FKBP12. These immunophilin-drug complexes interface with various intracellular signal transduction systems, especially in the immune and nervous systems.

Immunophilins are known to have peptidyl-prolyl isomerase (PPIase), or rotamase, enzyme activity. It has been determined that rotamase enzyme activity plays a role in the catalyzation of the interconversion of the cis and trans isomers of peptide and protein substrates for the immunophilin proteins.

Immunophilins were originally discovered and studied in the immune tissue. It was initially postulated by those skilled in the art that inhibition of the immunophilins' rotamase activity leads to inhibition of T-cell proliferation, thereby causing the immunosuppressive activity exhibited by immunosuppressant drugs, such as cyclosporin A, FK506, and rapamycin. Further study has shown that the inhibition of rotamase activity, in and of itself, does not result in immunosuppressive activity. Schreiber et al., *Science*, 1990, vol. 250, pp. 556–559. Instead, immunosuppression appears to stem from the formation of a complex of immunosuppressant drugs with immunophilins. It has been shown that the immunophilin-drug complexes interact with ternary protein targets as their mode of action. Schreiber et al., *Cell*, 1991, vol. 66, pp. 807–815. In the case of FKBP-FK506 and cyclophilin-CsA, the immunophilin-drug complex binds to the enzyme calcineurin and inhibits the T-cell receptor signaling necessary to T-cell proliferation. Similarly, the immunophilin-drug complex of FKBP-rapamycin interacts with the RAFT1/FRAP protein and inhibits the IL-2 receptor signaling also necessary to T-cell proliferation. In either case, T-cell proliferation is inhibited.

In addition to immune tissues, immunophilins have also been found in the central nervous system. Immunophilin concentrations are 10–50 times greater in the central nervous system than in the immune system. Within neural tissues, immunophilins appear to influence nitric oxide synthesis, neurotransmitter release, and neuronal process extension.

It has been found that picomolar concentrations of immunosuppressants such as FK506 and rapamycin stimulate neurite outgrowth in PC12 cells and sensory neurons such as dorsal root ganglion cells (DRGs) Lyons et al., *Proc. of Natl. Acad. Sci.*, 1994, vol. 91, pp. 3191–3195. In whole animal experiments, FK506 has been shown to stimulate nerve regeneration following facial nerve injury.

However, when administered chronically, immunosuppressant drugs exhibit a number of potentially serious side effects including nephrotoxicity, such as impairment of glomerular filtration and irreversible interstitial fibrosis (Kopp et al., *J. Am. Soc. Nephrol.*, 1991, 1:162); neurological deficits, such as involuntary tremors, or non-specific cerebral angina, such as non-localized headaches (De Groen et al., *N. Engl. J. Med.*, 1987, 317:861); and vascular hypertension with complications resulting therefrom (Kahan et al., *N. Engl. J. Med.*, 1989, 321:1725).

Surprisingly, it has been found that certain compounds with a high affinity for FKBPs are potent rotamase inhibitors and exhibit excellent neurotrophic effects, but are devoid of immunosuppressive activity. These findings suggest the use of rotamase inhibitors in treating various peripheral neuropathies and enhancing neuronal regrowth in the central nervous system (CNS).

Studies have demonstrated that neurodegenerative disorders, such as Alzheimer's disease, Parkinson's disease and amyotrophic lateral sclerosis (ALS), may occur due to the loss, or decreased availability, of a neurotrophic substance specific for a particular population of neurons affected in the disorder.

Several neurotrophic factors affecting specific neuronal populations in the central nervous system have been identified. For example, it has been hypothesized that Alzheimer's disease results from a decrease or loss of nerve growth factor (NGF). It has thus been proposed to treat SDAT patients with exogenous nerve growth factor or other neurotrophic proteins, such as brain derived growth factor, glial derived growth factor, ciliary neurotrophic factor and neurotropin-3, to increase the survival of degenerating neuronal populations.

The present invention provides compounds containing small molecule FKBP rotamase inhibitors for enhancing neurite outgrowth, and promoting neuronal growth and regeneration in various neuropathological situations where neuronal repair can be facilitated, including: peripheral nerve damage caused by physical injury or disease state such as diabetes; physical damage to the central nervous system (spinal cord and brain); brain damage associated with stroke; and neurological disorders relating to neurodegeneration, such as Parkinson's disease, SDAT (Alzheimer's disease) and amyotrophic lateral sclerosis. The inventive compounds are also useful for treating alopecia, promoting hair growth, treating vision disorder, improving vision, treating memory impairment and enhancing memory performance in an animal.

SUMMARY OF THE INVENTION

The present invention relates to neurotrophic low molecular weight, small molecule cyclic ester and amide derivatives having an affinity for FKBP-type immunophilins. Once bound to these proteins, the compounds are potent inhibitors of the enzyme activity associated with immunophilin proteins, particularly peptidyl-prolyl isomerase, or rotamase, enzyme activity. The compounds may or may not exert immunosuppressive activity.

Specifically, the present invention relates to a compound of formula I

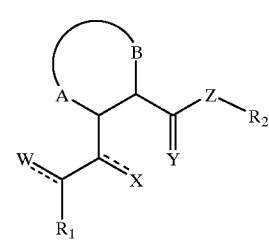

or a pharmaceutically acceptable salt, ester, or solvate thereof, wherein:

A and B, taken together with the carbon atoms to which they are respectively attached, form a 5–7 membered saturated or unsaturated carbocyclic or heterocyclic ring, said heterocyclic ring containing one or more heteroatom(s) independently selected from the group consisting of O, S, SO, $SO_2$, N, NH, and NR;

R, $R_1$, and $R_2$ are independently $C_1$–$C_9$ straight or branched chain alkyl, $C_2$–$C_9$ straight or branched chain alkenyl, $C_3$–$C_9$ cycloalkyl, $C_3$–$C_9$ cycloalkenyl, or Ar, wherein said R, $R_1$, and $R_2$ are independently unsubstituted or substituted with one or substituent(s);

Ar is an aromatic, mono-, bi- or tricyclic, carbo- or heterocyclic ring having an individual ring size of 5–9 members, said heterocyclic ring containing one or more heteroatom(s) independently selected from the group consisting of O, S, SO, $SO_2$, N, NH and NR;

W and X are independently O, S, $CH_2$ or $H_2$;

Y is O or S; and

Z is O, NH or NR.

A preferred embodiment of this invention is a compound of formula II

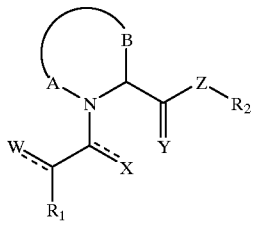

II or a pharmaceutically acceptable salt, ester, or solvate thereof, wherein:

A and B, taken together with the nitrogen and carbon atoms to which they are respectively attached, form a 5–7 membered saturated or unsaturated heterocyclic ring containing one or more heteroatom(s) independently selected from the group consisting of O, S, SO, $SO_2$, N, NH and NR;

R and $R_1$ are independently $C_1$–$C_9$ straight or branched chain alkyl, $C_2$–$C_9$ straight or branched chain alkenyl, $C_3$–$C_9$ cycloalkyl, $C_3$–$C_9$ cycloalkenyl, or Ar, wherein said R and $R_1$ are independently unsubstituted or substituted with one or more substituent(s);

$R_2$ is $C_3$–$C_9$ cycloalkyl, $C_3$–$C_9$ cycloalkenyl or Ar, wherein said cycloalkyl or cycloalkenyl is unsubstituted or substituted with one or more substituent(s), or said Ar is substituted with one or more substituent(s);

Ar is an aromatic, mono-, bi- or tricyclic, carbo- or heterocyclic ring having an individual ring size of 5–9 members, said heterocyclic ring containing one or more heteroatom(s) independently selected from the group consisting of O, S, SO, $SO_2$, N, NH and NR;

W and X are independently O, S, $CH_2$ or $H_2$;

Y is O or S; and

Z is O, NH or NR.

Another preferred embodiment is a compound of formula III

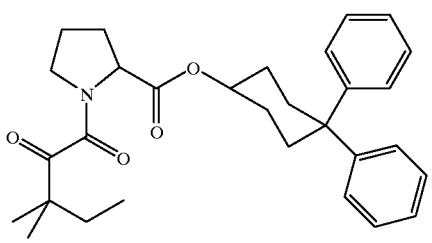

III or a pharmaceutically acceptable salt, ester, or solvate thereof.

The present invention also relates to a pharmaceutical composition comprising an effective amount of the compound of formula I, II or III, and a pharmaceutically acceptable carrier.

The present invention further relates to a method of effecting a neuronal activity in an animal, comprising administering to said animal an effective amount of the compound of formula I, II or III.

DETAILED DESCRIPTION OF THE INVENTION

Definitions

"Alkyl" means a branched or unbranched saturated hydrocarbon chain containing 1 to 6 carbon atoms, such as methyl, ethyl, propyl, iso-propyl, butyl, iso-butyl, tert-butyl, n-pentyl, n-hexyl, and the like, unless otherwise indicated.

"Alkoxy" means the group —OR wherein R is alkyl as herein defined. Preferably, R is a branched or unbranched saturated hydrocarbon chain containing 1 to 3 carbon atoms.

"Alopecia" refers to deficient hair growth and partial or complete loss of hair, including without limitation androgenic alopecia (male pattern baldness), toxic alopecia, alopecia senilis, alopecia areata, alopecia pelada and trichotillomania. Alopecia results when the pilar cycle is disturbed. The most frequent phenomenon is a shortening of the hair growth or anagen phase due to cessation of cell proliferation. This results in an early onset of the catagen phase, and consequently a large number of hairs in the telogen phase during which the follicles are detached from the dermal papillae, and the hairs fall out. Alopecia has a number of etiologies, including genetic factors, aging, local and systemic diseases, febrile conditions, mental stresses, hormonal problems, and secondary effects of drugs.

"Enhancing memory performance" refers to improving or increasing the mental faculty by which to register, retain or recall past experiences, knowledge, ideas, sensations, thoughts or impressions.

"Eye" refers to the anatomical structure responsible for vision in humans and other animals, and encompasses the following anatomical structures, without limitation: lens, vitreous body, ciliary body, posterior chamber, anterior chamber, pupil, cornea, iris, canal of Schlemm, zonules of Zinn, limbus, conjunctiva, choroid, retina, central vessels of the retina, optic nerve, fovea centralis, macula lutea, and sclera.

"Halo" means fluoro, chloro, bromo, or iodo, unless otherwise indicated.

"Isomers" refer to different compounds that have the same molecular formula. "Stereoisomers" are isomers that differ only in the way the atoms are arranged in space. "Enantiomers" are a pair of stereoisomers that are non-superimposable mirror images of each other. "Diastereoisomers" are stereoisomers which are not mirror images of each other. "Racemic mixture" means a mixture containing equal parts of individual enantiomers. "Non-racemic mixture" is a mixture containing unequal parts of individual enantiomers or stereoisomers.

"Memory impairment" refers to a diminished mental registration, retention or recall of past experiences, knowledge, ideas, sensations, thoughts or impressions. Memory impairment may affect short and long-term information retention, facility with spatial relationships, memory (rehearsal) strategies, and verbal retrieval and production. Common causes of memory impairment are age, severe head trauma, brain anoxia or ischemia, alcoholic-nutritional diseases, and drug intoxications. Examples of memory impairment include, without limitation, benign forgetfulness, amnesia and any disorder in which memory deficiency is present, such as Korsakoff's amnesic psychosis, dementia and learning disorders.

"Ophthalmological" refers to anything about or concerning the eye, without limitation, and is used interchangeably with "ocular," "ophthalmic," "ophthalmologic," and other such terms, without limitation.

"Pharmaceutically acceptable salt, ester, or solvate" refers to a salt, ester, or solvate of a subject compound which possesses the desired pharmacological activity and which is neither biologically nor otherwise undesirable. A salt, ester, or solvate can be formed with inorganic acids such as acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, gluconate, glycerophosphate, hemisulfate, heptanoate, hexanoate, hydrochloride, hydrobromide, hydroiodide, 2-hydroxyethanesulfonate, lactate, maleate, methanesulfonate, naphthylate, 2-naphthalenesulfonate, nicotinate, oxalate, sulfate, thiocyanate, tosylate and undecanoate. Examples of base salts, esters, or solvates include ammonium salts; alkali metal salts, such as sodium and potassium salts; alkaline earth metal salts, such as calcium and magnesium salts; salts with organic bases, such as dicyclohexylamine salts; N-methyl-D-glucamine; and salts with amino acids, such as arginine, lysine, and so forth. Also, the basic nitrogen-containing groups can be quarternized with such agents as lower alkyl halides, such as methyl, ethyl, propyl, and butyl chlorides, bromides, and iodides; dialkyl sulfates, such as dimethyl, diethyl, dibutyl, and diamyl sulfates; long chain halides, such as decyl, lauryl, myristyl, and stearyl chlorides, bromides, and iodides; aralkyl halides, such as benzyl and phenethyl bromides; and others. Water or oil-soluble or dispersible products are thereby obtained.

"Phenyl" includes all possible isomeric phenyl radicals, optionally monosubstituted or multi-substituted with substituents selected from the group consisting of alkyl, alkoxy, hydroxy, halo, and haloalkyl.

"Pilar cycle" refers to the life cycle of hair follicles, and includes three phases:

(1) the anagen phase, the period of active hair growth which, insofar as scalp hair is concerned, lasts about three to five years;

(2) the catagen phase, the period when growth stops and the follicle atrophies which, insofar as scalp hair is concerned, lasts about one to two weeks; and (3) the telogen phase, the rest period when hair progressively separates and finally falls out which, insofar as scalp hair is concerned, lasts about three to four months.

Normally 80 to 90 percent of the follicles are in the anagen phase, less than 1 percent being in the catagen phase, and the rest being in the telogen phase. In the telogen phase, hair is uniform in diameter with a slightly bulbous, non-pigmented root. By contrast, in the anagen phase, hair has a large colored bulb at its root.

"Preventing vision degeneration" as used herein includes the ability to prevent degeneration of vision in patients newly diagnosed as having a degenerative disease affecting vision, or at risk of developing a new degenerative disease affecting vision, and for preventing further degeneration of vision in patients who are already suffering from or have symptoms of a degenerative disease affecting vision.

"Promoting hair growth" refers to maintaining, inducing, stimulating, accelerating, or revitalizing the germination of hair.

"Promoting vision regeneration" refers to maintaining, improving, stimulating or accelerating recovery of, or revitalizing one or more components of the visual system in a manner which improves or enhances vision, either in the presence or absence of any ophthalmologic disorder, disease, or injury.

"Treating" refers to:

(i) preventing a disease and/or condition from occurring in a subject which may be predisposed to the disease and/or condition but has not yet been diagnosed as having it;

(ii) inhibiting the disease and/or condition, i.e., arresting its development; or (iii) relieving the disease and/or condition, i.e., causing regression of the disease and/or condition.

"Treating alopecia" refers to:

(i) preventing alopecia in an animal which may be predisposed to alopecia; and/or (ii) inhibiting, retarding or reducing alopecia; and/or (iii) promoting hair growth; and/or (iv) prolonging the anagen phase of the hair cycle; and/or (v) converting vellus hair to growth as terminal hair. Terminal hair is coarse, pigmented, long hair in which the bulb of the hair follicle is seated deep in the dermis. Vellus hair, on the other hand, is fine, thin, non-pigmented short hair in which the hair bulb is located superficially in the dermis. As alopecia progresses, the hairs change from the terminal to the vellus type.

"Vision", as used herein, refers to the ability of humans and other animals to process images, and is used interchangeably with "sight", "seeing", and other such terms, without limitation.

"Vision disorder" refers to any disorder that affects or involves vision, including without limitation visual impairment, orbital disorders, disorders of the lacrimal apparatus, disorders of the eyelids, disorders of the conjunctiva, disorders of the cornea, cataracts, disorders of the uveal tract, disorders of the retina, disorders of the optic nerve or visual pathways, free radical induced eye disorders and diseases, immunologically-mediated eye disorders and diseases, eye injuries, and symptoms and complications of eye disease, eye disorder, or eye injury.

"Visual impairment" refers to any dysfunction in vision including without limitation disturbances or diminution in vision (e.g., binocular, central, peripheral, scotopic), visual acuity for objects near and for, visual field, ocular motility, color perception, adaptation to light and dark, accommodation, refraction, and lacrimation. See *Physicians' Desk Reference (PDR) for Ophthalmology*, 16th Edition, 6:47 (1988).

Compounds of the Invention

The low molecular weight, small molecule FKBP inhibitor compounds of this invention have an affinity for FKBP-type immunophilins, such as FKBP12. When the compounds of this invention are bound to an FKBP-type immunophilin, they have been found to inhibit the prolyl-peptidyl cis-trans isomerase activity, or rotamase, activity of the binding protein. Unexpectedly, the compounds are effective in stimulating neurite growth, as well as treating alopecia, promoting hair growth, treating vision disorders, improving vision, treating memory impairment, and enhancing memory performance in an animal. The compounds may or may not be immunosuppressive.

FORMULA I

The cyclic ester or amide derivative may be a compound of formula I

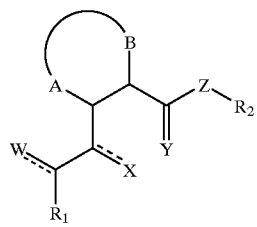

I or a pharmaceutically acceptable salt, ester, or solvate thereof, wherein:

A and B, taken together with the carbon atoms to which they are attached, form a 5–7 membered saturated or unsaturated carbocyclic or heterocyclic ring, said heterocyclic ring containing one or more heteroatom(s) independently selected from the group consisting of O, S, SO, SO$_2$, N, NH, and NR;

R, R$_1$ and R$_2$ are independently C$_1$–C$_9$ straight or branched chain alkyl, C$_2$–C$_9$ straight or branched chain alkenyl, C$_3$–C$_9$ cycloalkyl, C$_3$–C$_9$ cycloalkenyl, or Ar, wherein said R, R$_1$ and R$_2$ are independently unsubstituted or substituted with one or more substituent(s) and the carbon atoms of said alkyl, alkenyl, cycloalkyl, and cycloalkenyl are independently unsubstituted or substituted with one or more heteroatom(s);

Ar is an aromatic, mono-, bi- or tricyclic, carbo- or heterocyclic ring having an individual ring size of 5–9 members, said heterocyclic ring containing one or more heteroatom(s) independently selected from the group consisting of O, S, SO, SO$_2$, N, NH and NR;

W and X are independently O, S, CH$_2$ or H$_2$;

Y is O or S; and

Z is O, NH, or NR.

FORMULA II

In a preferred embodiment, the cyclic ester or amide derivative is a compound of formula II

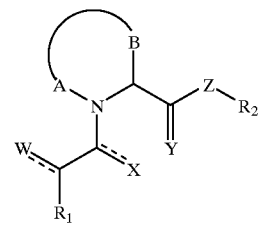

II or a pharmaceutically acceptable salt, ester, or solvate thereof, wherein:

A and B, taken together with the nitrogen and carbon atoms to which they are respectively attached, form a 5–7 membered saturated or unsaturated heterocyclic ring containing one or more heteroatom(s) independently selected from the group consisting O, S, SO, SO$_2$, N, NH and NR;

R and R, are independently C$_1$–C$_9$ straight or branched chain alkyl, C$_2$–C$_9$ straight or branched chain alkenyl, C$_3$–C$_9$ cycloalkyl, C$_3$–C$_9$ cycloalkenyl, or Ar, wherein said R and R$_1$ are independently unsubstituted or substituted with one or more substituent(s), and the carbon atoms of said alkyl, alkenyl, cycloalkyl, and cycloalkenyl are independently unsubstituted or substituted with one or more heteroatom(s);

R$_2$ is C$_3$–C$_9$ cycloalkyl, C$_3$–C$_9$ cycloalkenyl or Ar, wherein said R$_2$ is unsubstituted or substituted with one or more substituent(s), and the carbon atoms of said cycloalkyl and cycloalkenyl are independently substituted with one or more heteroatom(s);

Ar is an aromatic, mono-, bi- or tricyclic, carbo- or heterocyclic ring having an individual ring size of 5–9 members, said heterocyclic ring containing one or more heteroatom(s) independently selected from the group consisting of O, S, SO, SO$_2$, N, NH and NR;

W and X are independently O, S, CH$_2$ or H$_2$;

Y is O or S; and

Z is O, NH or NR.

In another preferred embodiment, R$_2$ is substituted with (Ar) n, and n is 1–2.

FORMULA III

In the most preferred embodiment, the cyclic ester or amide derivative is 4,4-diphenylcyclohexl (2S)-1-(3,3-dimethyl-2-oxopentanoyl)-pyrrolidine-2-carboxylate, a compound of formula III

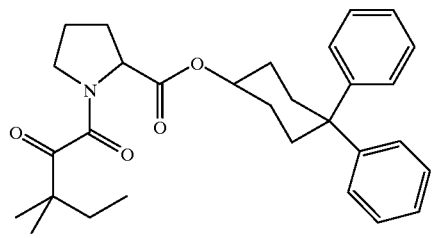

III or a pharmaceutically acceptable salt, ester, or solvate thereof.

In the compounds of formulas I-III, possible substituents of R, R$_1$ and R$_2$ are C$_1$–C$_9$ straight or branched chain alkyl, $C_2$–$C_9$ straight or branched chain alkenyl, $C_1$–$C_9$ alkoxy, $C_2$–$C_9$ alkenyloxy, phenoxy, benzyloxy, $C_3$–$C_8$ cycloalkyl, $C_5$–$C_7$ cycloalkenyl, hydroxy, carboxy, carbonyl, amino, amido, cyano, isocyano, nitro, nitroso, nitrilo, isonitrilo, imino, azo, diazo, sulfonyl, sulfoxy, thio, thiocarbonyl, thiocyano, formanilido, thioformamido, sulfhydryl, halo, haloalkyl, trifluoromethyl, and carbocyclic and heterocyclic moieties. Carbocyclic moieties include alicyclic and aromatic structures.

Examples of useful carbocyclic and heterocyclic moieties include, without limitation, phenyl, benzyl, naphthyl, indenyl, azulenyl, fluorenyl, anthracenyl, indolyl, isoindolyl, indolinyl, benzofuranyl, benzothiophenyl, indazolyl, benzimidazolyl, benzthiazolyl, tetrahydrofuranyl, tetrahydropyranyl, pyridyl, pyrrolyl, pyrrolidinyl, pyridinyl, pyrimidinyl, purinyl, quinolinyl, isoquinblinyl, tetrahydroquinolinyl, quinolizinyl, furyl, thiophenyl, imidazolyl, oxazolyl, benzoxazolyl, thiazolyl, isoxazolyl, isotriazolyl, oxadiazolyl, triazolyl, thiadiazolyl, pyridazinyl, pyrimidinyl, pyrazinyl, triazinyl, trithianyl, indolizinyl, pyrazolyl, pyrazolinyl, pyrazolidinyl, thienyl, tetrahydroisoquinolinyl, cinnolinyl, phthalazinyl, quinazolinyl, quinoxalinyl, naphthyridinyl, pteridinyl, carbazolyl, acridinyl, phenazinyl, phenothiazinyl, and phenoxazinyl.

All the compounds of formulas I-III possess asymmetric centers and thus can be produced as mixtures of stereoisomers or as individual R- and S-stereoisomers. The individual stereoisomers may be obtained by using an optically active starting material, by resolving a racemic or non-racemic mixture of an intermediate at some appropriate stage of the synthesis, or by resolving the compounds of formulas I-III. It is understood that the compounds of formulas I-III encompass individual stereoisomers as well as mixtures (racemic and non-racemic) of stereoisomers. S-stereoisomers are most preferred.

Pharmaceutical Compositions of the Invention

The present invention also relates to a pharmaceutical composition comprising:

(i) an effective amount of a compound of formula I, II or III; and (ii) a pharmaceutically acceptable carrier.

Preferred compounds of formula I and II are set forth above.

In a preferred embodiment of the inventive pharmaceutical composition, the amount of the compound of formula I, II or III is effective for binding to an FKBP-type immunophilin.

In another preferred embodiment, the amount of the compound of formula I, II or III is effective for effecting a neuronal activity in an animal.

Methods of the Invention

The compounds of the present invention have an affinity for the FK506 binding protein, particularly FKBP12, which is present in the brain. When the inventive compounds bind to FKBP in the brain, they exhibit excellent neurotrophic activity. This activity is useful in the stimulation of damaged neurons, the promotion of neuronal regeneration, the prevention of neurodegeneration, and the treatment of several neurological disorders known to be associated with neuronal degeneration and peripheral neuropathies.

For the foregoing reasons, the present invention further relates to a method of effecting a neuronal activity in an animal, comprising administering to said animal an effective amount of a compound of formula I, II or III.

Preferred compounds of formula I and II are set forth above.

In a preferred embodiment, the neuronal activity is selected from the group consisting of stimulation of damaged neurons, promotion of neuronal regeneration, prevention of neurodegeneration and treatment of neurological disorder.

The neurological disorders that may be treated include but are not limited to: trigeminal neuralgia; glossopharyngeal neuralgia; Bell's Palsy; myasthenia gravis; muscular dystrophy; amyotrophic lateral sclerosis; progressive muscular atrophy; progressive bulbar inherited muscular atrophy; herniated, ruptured or prolapsed invertebrate disk syndromes; cervical spondylosis; plexus disorders; thoracic outlet destruction syndromes; peripheral neuropathies such as those caused by lead, dapsone, ticks, porphyria or Guillain-Barré syndrome; Alzheimer's disease; and Parkinson's disease.

The compounds of the present invention are particularly useful for treating a neurological disorder selected from the group consisting of: peripheral neuropathy caused by physical injury or disease state, traumatic injury to the brain, physical damage to the spinal cord, stroke associated with brain damage, and neurological disorder relating to neurodegeneration. Examples of neurological disorders relating to neurodegeneration are Alzheimer's Disease, Parkinson's Disease and amyotrophic lateral sclerosis.

For these purposes, the compounds of the present invention may be administered orally, parenterally, by inhalation spray, topically, rectally, nasally, buccally, vaginally or via an implanted reservoir in dosage formulations containing conventional non-toxic pharmaceutically-acceptable carriers, adjuvants and vehicles. The term parenteral as used herein includes subcutaneous, intravenous, intramuscular, intraperitoneally, intrathecally, intraventricularly, intrasternal and intracranial injection or infusion techniques.

To be effective therapeutically as central nervous system targets the immunophilin-drug complex should readily penetrate the blood-brain barrier when peripherally administered. Compounds of this invention which cannot penetrate the blood-brain barrier can be effectively administered by an intraventricular route.

The compounds may be in the form of a sterile injectable preparation, for example as a sterile injectable aqueous or oleaginous suspension. This suspension may be formulated according to techniques know in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. Fatty acids such as oleic acid and its glyceride derivatives find use in the preparation of injectables, olive oil or castor oil, especially in their polyoxyethylated versions. These oil solutions or suspensions may also contain a long-chain alcohol diluent or dispersant.

Additionally, the compounds may be administered orally in the form of capsules or tablets, for example, or as an aqueous suspension or solution. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening and/or flavoring and/or coloring agents may be added.

The compounds of this invention may also be administered in the form of suppositories for rectal administration of the drug. These compositions can be prepared by mixing the drug with a suitable non-irritating excipient which is solid at room temperature but liquid at rectal temperature and therefore will melt in the rectum to release the drug. Such materials include cocoa butter, beeswax and polyethylene glycols.

The compounds of this invention may also be administered optically, especially when the conditions addressed for treatment involve areas or organs readily accessible by topical application, including neurological disorders of the eye, the skin, or the lower intestinal tract. Suitable topical formulations are readily prepared for each of these areas.

For ophthalmic use, the compounds can be formulated as micronized suspensions in isotonic, pH adjusted sterile saline, or, preferably, as solutions is isotonic, pH adjusted sterile saline, either with or without a preservative such as benzylalkonium chloride. Alternatively for the ophthalmic uses the compounds may be formulated in an ointment such as petrolatum.

For application topically to the skin, the compounds can be formulated in a suitable ointment containing the compound suspended or dissolved in, for example, a mixture with one or more of the following: mineral oil, liquid petrolatum, white petrolatum, propylene glycol, polyoxyethylene polyoxypropylene compound, emulsifying wax and water. Alternatively, the compounds can be formulated in a suitable lotion or cream containing the active compound suspended or dissolved in, for example, a mixture of one or more of the following: mineral oil, sorbitan monostearate, polysorbate 60, cetyl esters wax, cetearyl alcohol, 2-octyldodecanol, benzyl alcohol and water.

Topical application for the lower intestinal tract an be effected in a rectal suppository formulation (see above) or in a suitable enema formulation.

Dosage levels on the order of about 0.1 mg to about 10,000 mg. of the active ingredient compound are useful in the treatment of the above conditions, with preferred levels of about O.lmg to about 1,000 mg.

The amount of active ingredient that may be combined with the carrier materials to produce a single dosage form will vary depending upon the host treated and the particular mode of administration.

It is understood, however, that a specific dose level for any particular patient will depend upon a variety of factors including the activity of the specific compound employed, the age, body weight, general health, sex, diet, time of administration, rate of excretion, drug combination, and the severity of the particular disease being treated and form of administration.

The compounds can be administered with other neurotrophic agents such as neurotrophic growth factor (NGF), glial derived growth factor, brain derived growth factor, ciliary neurotrophic factor, and neurotropin-3. The dosage level of other neurotrophic drugs will depend upon the factors previously stated and the neurotrophic effectiveness of the drug combination.

$K_i$ Test Procedure

Inhibition of the peptidyl-prolyl isomerase (rotamase) activity of the inventive compounds can be evaluated by known methods described in the literature (Harding, M. W. et al. *Nature* 341: 758–760 (1989); Holt et al. *J. Am. Chem. Soc.* 115: 9923–9938). These values are obtained as apparent Ki's and are presented in Table I. The cis-trans isomerization of an alanine-proline bond in a model substrate, N-succinyl-Ala-Ala-Pro-Phe-p-nitroanilide, is monitored spectrophotometrically in a chymotrypsin-coupled assay, which releases para-nitroanilide from the trans form of the substrate. The inhibition of this reaction caused by the addition of different concentrations of inhibitor is determined, and the data is analyzed as a change in first-order rate constant as a function of inhibitor concentration to yield the apparent Kivalues.

In a plastic cuvette are added 950 mL of ice cold assay buffer (25 mM HEPES, pH 7.8, 100 mM NaCl), 10 mL of FKBP (2.5 mM in 10 mM Tris-Cl pH 7.5, 100 mM NaCl, 1 mM dithiothreitol), 25 mL of chymotrypsin (50 mg/mL in 1 mM HCl) and 10 mL of test compound at various concentrations in dimethyl sulfoxide. The reaction is initiated by the addition of 5 mL of substrate (succinyl-Ala-Phe-Pro-Phe-para-nitroanilide, 5 mg/mL in 2.35 mM LiCl in trifluoroethanol).

The absorbance at 390 nM versus time is monitored for 90 sec using a spectrophotometer and the rate constants are determined from the absorbance versus time data files.

Data for these experiments is presented in Table

TABLE I

| Compound | Ki (nM) |
|---|---|
| [structure] | 5638 |

In mammalian cells, FKBP-12 complexes with the inositol triphosphate receptor ($IP_3R$) and the ryanodine receptor (RyR). It is believed that the neurotrophic compounds of this invention disassociates FKBP-12 from these complexes causing the calcium channel to become "leaky" (Cameron et al., 1995). Calcium fluxes are involved in neurite extensions so that the $IP_3R$ receptor and the ryanodine receptor might be involved in the neurotrophic effects of drugs. Since the drugs bind to the same site as FKBP-12 as the $IP_3R$ receptor, one could assume that the drugs displace the channels from FKBP-12.

Chick Dorsal Root Ganglion

Cultures and Neurite Outgrowth

Dorsal root ganglia are dissected from chick embryos of ten day gestation. Whole ganglion explants are cultured on thin layer Matrigel-coated 12 well plates with Liebovitz L15 plus high glucose media supplemented with 2 mM glutamine and 10% fetal calf serum, and also containing 10 μM cytosine β-D arabinofuranoside (Ara C) at 37° C. in an environment containing 5% $CO_2$. Twenty-four hours later, the DRGs are treated with various concentrations of nerve growth factor (NGF), immunophilin ligands, or combinations of NFG plus drugs. Forty-eight hours after drug treatment, the ganglia are visualized under phase contrast or Hoffman Modulation contrast with a Zeiss Axiovert inverted microscope. Photomicrographs of the explants are made, and neurite outgrowth is quantitated. Neurites longer than the DRG diameter are counted as positive, with total number of neurites quantitated per each experimental condition. Three to four DRGs are cultured per well, and each treatment is performed in duplicate. The compounds of the present invention promote neurite outgrowth in sensory neurons.

Sciatic Nerve Axotomy

Six-week old male Sprague-Dawley rats are anesthetized, and the sciatic nerve exposed and crushed, at the level of the hip, by forceps. Test compounds or vehicle are administered subcutaneously just prior to the lesion and daily for the following 18 days. Sections of the sciatic nerve are stained with Holmes silver stain to quantify the number of axons, and Luxol fast blue to quantify the level of myelination. Eighteen days after lesion, there is a significant decrease in the number of axons (50% decrease as compared to non-lesioned control) and degree of myelination (90% decrease as compared to non-lesioned control) in animals treated with vehicle.

Administration of neuroimmunophilin FKBP ligands, which are compounds related to those of the present invention, just prior to the lesion and daily for 18 days following the lesion, results in significant regeneration of both axon number and the degree of myelination as compared to vehicle treated animals. The significant efficacy of neuroimmunophilin FKBP ligands is consistent with their potent activity in inhibiting rotamase activity and stimulating neurite outgrowth in chick DRGs.

MPTP Model of Parkinson's Disease in Mice The neurotrophic effects of the compounds of the present invention are further demonstrated in an animal model of neurodegenerative disease: MPTP lesioning of dopaminergic neurons in mice is used as an animal model of Parkinson's Disease. Four week old male CD1 white mice are dosed i.p. with 30 mg/kg of MPTP for 5 days. A cyclic ester or amide derivative (10–40 mg/kg), or vehicle, is administered s.c. along with the MPTP for 5 days, as well as for an additional 5 days following cessation of MPTP treatment. At 18 days following MPTP treatment, the animals are sacrificed and the striata are dissected and homogenized. Binding of [3H] CFT, a radioligand for the dopamine transporter, to the stiatal membranes is done to quantitate the level of the dopamine transporter (DAT) following lesion and drug treatment. Immunostaining is performed on saggital and coronal brain sections using anti-tyrosine hydoxylase Ig to quantitate survival and recovery of dopaminergic neurons. In animals treated with MPTP and vehicle, a substantial loss of functional dopaminergic terminals is observed as compared to non-lesioned animals. Lesioned animals receiving cyclic ester or amide derivatives show a nearly quantitative recovery of TH-stained dopaminergic neurons.

These experiments demonstrate the significant recovery in functional dopaminergic terminals, as assayed by [3H]-CFT binding, relative to animals receiving MPTP but not a cyclic ester or amide derivative. Animals receiving 40 mg/kg of cyclic ester or amide derivative in addition to MPTP manifest greater recovery of [3H]-CFT binding. Immunostaining for tyrosine hydroxylase (a marker of viable dopaminergic neurons) in the striatum, the nigra, and the medial forebrain bundle, shows a clear and marked recovery of functional neurons in animals that receive a cyclic ester or amide derivative, as compared to animals that received lesioning agent but no drug (MPTP/Vehicle).

Data on Related Compounds

U.S. patent application Ser. No. 09/089,416, filed Jun. 3, 1998 is incorporated herein by reference. Said application includes $K_i$ data for various neuroimmunophilin FKBP ligands, which are related to the compounds of the present invention (see Tables IX–XVI).

U.S. patent application Ser. No. 08/479,436, filed Jun. 7, 1995, is also incorporated herein by reference. Said application includes neurite outgrowth and MPTP recovery data for various neuroimmunophilin FKBP ligands, which are related to the compounds of the present invention (see Table II and FIGS. 4–8, respectively).

U.S. patent application Ser. No. 08/719,947, filed Sep. 25, 1996, is further incorporated herein by reference. Said application includes neurite outgrowth data for various neuroimmunophilin FKBP ligands, which are related to the compounds of the present invention (see Table III, FIGS. 1(A–C), and FIGS. 2(A–C)).

EXAMPLES

The following examples are illustrative of the present invention and are not intended to be limitations thereon. Unless otherwise indicated, all percentages are based on 100% by weight of the final compound or composition.

The compounds of the present invention can be readily prepared by standard techniques of organic chemistry, utilizing the general synthetic pathway depicted below in Scheme I. Precursor compounds can be prepared by methods known to those skilled in the art.

Scheme I
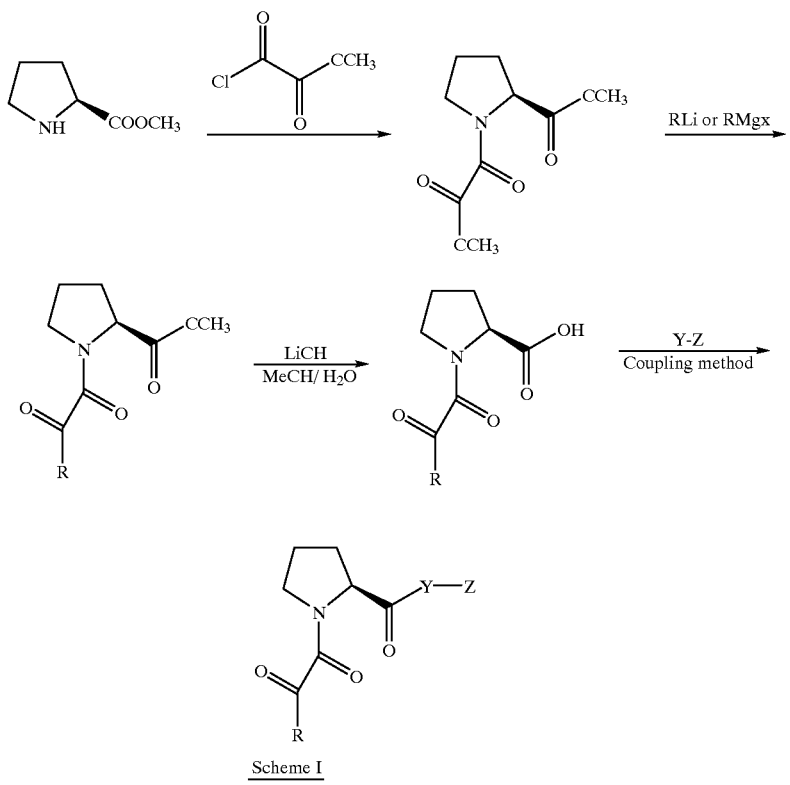
Scheme I
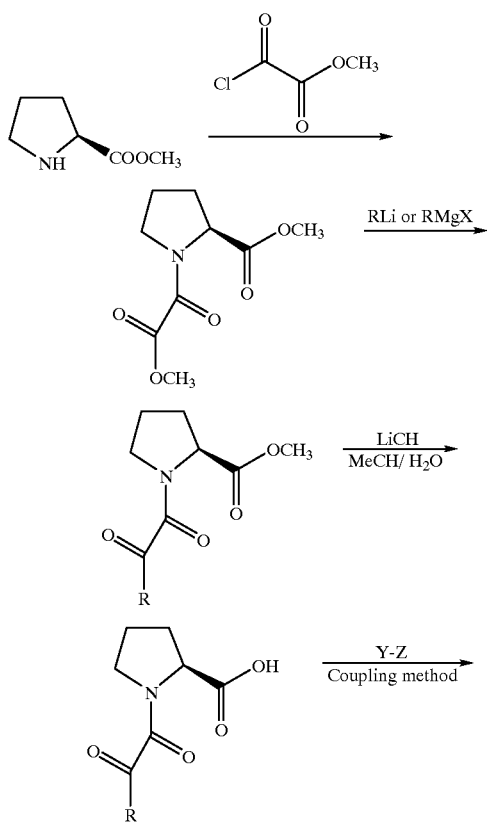

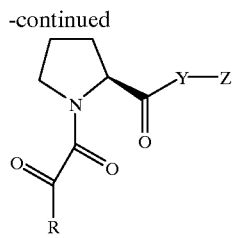

Example 1

Synthesis of 4,4-Diphenylcyclohexl (2S)-1-(3,3-dimethyl-2-oxopentanoyl)-pyrrolidine-2-carboxylate (Formula III)

1. Synthesis of methyl (2S)-1-(1,2-dioxo-2-methoxy ethyl)-2-pyrrolidinecarboxylate.

A solution of L-proline methyl ester hydrochloride (3.08 g; 18.60 mmol) in dry methylene chloride was cooled to 0° C. and treated with triethylamine (3.92 g; 38.74 mmol; 2.1 eq). After stirring the formed slurry under a nitrogen atmosphere for 15 min, a solution of methyl oxalyl chloride (3.20 g; 26.12 mmol) in methylene chloride (45 mL) was added dropwise. The resulting mixture was stirred at 0° C. for 1.5 hr. After filtering to remove solids, the organic phase was washed with water, dried over $MgSO_4$ and concentrated. The crude residue was purified on a silica gel column, eluting with 50% ethyl acetate in hexane, to obtain 3.52 g (88%) of the product as a reddish oil. Mixture of cis-trans amide rotamers; data for trans rotamer given. $^1$H NMR ($CDCl_3$): d 1.93 (dm, 2H); 2.17 (m, 2H); 3.62 (m, 2H); 3.71 (s, 3H); 3.79, 3.84 (s, 3H total); 4.86 (dd, 1H, J=8.4, 3.3).

2. Synthesis of methyl (2S)-1-(1,2-dioxo-3,3-dimethylpentyl)-2-pyrrolidinecarboxylate.

A solution of methyl (2S)-l-(1,2-dioxo-2-methoxyethyl)-2-pyrrolidinecarboxylate (2.35 g; 10.90 mmol) in 30 mL of tetrahydrofuran (THF) was cooled to −78° C. and treated with 14.2 mL of a 1.0 M solution of 1,1-dimethylpropylmagnesium chloride in THF. After stirring the resulting homogeneous mixture at −78° C. for three hours, the mixture was poured into saturated ammonium chloride (100 mL) and extracted into ethyl acetate. The organic phase was washed with water, dried, and concentrated, and the crude material obtained upon removal of the solvent was purified on a silica gel column, eluting with 25% ethyl acetate in hexane, to obtain 2.10 g (75%) of the oxamate as a colorless oil. IH NMR ($CDCl_3$): d 0.88 (t, 3H); 1.22, 1.26 (s, 3H each); 1.75 (dm, 2H); 1.87–2.10 (m, 3H); 2.23 (m, 1H); 3.54 (m, 2H); 3.76 (s, 3H); 4.52 (dm, 1H, J=8.4, 3.4).

3. Synthesis of (2S)-1-(1,2-dioxo-3,3-dimethylnentyl)-2-pyrrolidinecarboxylic acid.

A mixture of methyl (2S)-1-(1,2-dioxo-3,3-dimethylpentyl)-2-pyrrolidinecarboxylate (2.10 g; 8.23 mmol), 1 N LIOH (15 mL), and methanol (50 mL) was stirred at 0° C. for 30 min and at room temperature overnight. The mixture was acidified to pH 1 with 1 N $HC_1$, diluted with water, and extracted into 100 mL of methylene chloride. The organic extract was washed with brine and concentrated to deliver 1.73 g (87%) of snow-white solid which did not require further purification. $^1$H NMR ($CDCl_3$): d 0.87 (t, 3H); 1.22, 1.25 (s, 3H each); 1.77 (dm, 2H); 2.02 (m, 2H); 2.17 e:(, 1H); 2.25 (m, 1H); 3.53 (dd, 2H, J=10.4, 7.3); 4.55 (dd, 1H, J=8.6, 4.1).

4. Synthesis of 4,4-Diphenylcyclohexl (2S)-1-(3,3-dimethyl-2-oxopentanoyl)-pyrrolidine-2-carboxylate (Formula III).

A mixture of (2S)-1-(1,2-dioxo-3,3-dimethylpentyl)-2-pyrrolidine-carboxylic acid (600 mg; 2.49 mmol), 4,4-diphenylcyclohexanol (942 mg; 3.73 mmol), dicyclohexyl-carbodiimide (822 mg; 3.98 mmol), camphorsulphonic acid (190 mg; 0.8 mmol) and 4-dimethylaminopyridine (100 mg; 0.8 mmol) in methylene chloride (20 mL) was stirred overnight under a nitrogen atmosphere. The reaction mixture was filtered through Celite to remove solids and concentrated in vacuo, and the crude material was purified on a flash column (25% ethyl acetate in hexane) to obtain the compound of Formula III as a white solid, m.p. 127.5–128.8° C. $^1$H NMR ($CDCl_3$, 400MHz): δ0.84 (t, 3H, J=7.5); 1.26, 1.28 (s, 3H each); 2.01–2.56 (m, 1OH); 2.15–2.28 (m, 2H); 2.48–2.67 (m, 2H); 3.42–3.68 (m, 2H); 4.48 (1H, dd, J=3.6, 8.5); 4.96 (m, 1H); 7.25–7.34 (m, 10H).

Example 2

A patient is suffering from peripheral nerve damage caused by physical injury or disease state such as diabetes. A cyclic ester or amide derivative as identified above, or a pharmaceutical composition comprising the same, may be administered to the patient. Enhanced neurite outgrowth, and neuronal growth and regeneration are expected to occur following treatment.

Example 3

A patient is suffering from physical damage to the central nervous system (spinal cord and brain). A cyclic ester or amide derivative as identified above, or a pharmaceutical composition comprising the same, may be administered to the patient. Enhanced neurite outgrowth, and neuronal growth and regeneration are expected to occur following treatment.

Example 4

A patient is suffering from brain damage associated with stroke. A cyclic ester or amide derivative as identified above, or a pharmaceutical composition comprising the same, may be administered to the patient. Enhanced neurite outgrowth, and neuronal growth and regeneration are expected to occur following treatment.

Example 5

A patient is suffering from neurodegeneration resulting from Parkinson's disease. A cyclic ester or amide derivative as identified above, or a pharmaceutical composition comprising the same, may be administered to the patient. Enhanced neurite outgrowth, and neuronal growth and regeneration are expected to occur following treatment.

Example 6

A patient is suffering from neurodegeneration resulting from amyotrophic lateral sclerosis. A cyclic ester or amide derivative as identified above, or a pharmaceutical composition comprising the same, may be administered to the patient. Enhanced neurite outgrowth, and neuronal growth and regeneration are expected to occur following treatment.

Example 7

A patient is suffering from neurodegeneration resulting from SDAT (Alzheimer's disease). A cyclic ester or amide derivative as identified above, or a pharmaceutical composition comprising the same, may be administered to the patient. Enhanced neurite outgrowth, and neuronal growth and regeneration are expected to occur following treatment.

The invention being thus described, it will be obvious that the same may be varied in many ways. Such variations are not to be regarded as a departure from the spirit and scope of the invention and all such modifications are intended to be included within the scope of the following claims.

We claim:

1. A compound of formula II

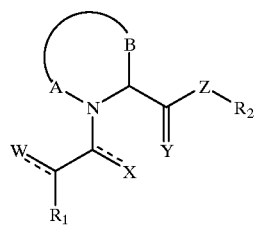

II or a pharmaceutically acceptable salt, ester, or solvate thereof, wherein:

A and B, taken together with the carbon atoms to which they are respectively attached, form a 5 membered saturated or unsaturated heterocyclic ring having one nitrogen heteroatom;

R and $R_1$ are independently $C_1$–$C_9$ straight or branched chain alkyl, $C_2$–$C_9$ straight or branched chain alkenyl, $C_3$–$C_9$ cycloalkyl, $C_3$–$C_9$ cycloalkenyl, or Ar,
wherein said R and $R_1$ are independently unsubstituted or substituted with one or more substituent(s) and the carbon atoms of said alkyl, alkenyl, cycloalkyl, and cycloalkenyl are independently unsubstituted or substituted with one or more heteroatom(s);

$R_2$ is $C_3$–$C_9$ cycloalkyl, $C_3$–$C_9$ cycloalkenyl or Ar,
wherein said cycloalkyl, cycloalkenyl, or Ar is substituted with one or more substituent(s), and the carbon atoms of said cycloalkyl and cycloalkenyl are independently unsubstituted or substituted with one or more heteroatom(s);

Ar is an aromatic or carbocyclic ring having an individual ring size of 5–9 members, or a mono-, bi- or tricyclic, heterocyclic ring having an individual ring size of 5–9 members,
said heterocyclic ring containing one or more heteroatom(s) independently selected from the group consisting of O, S, SO, $SO_2$, N, NH and NR;

W is O, S, $CH_2$ or $H_2$;

X is O or S;

Y is O or S; and

Z is O, NH or NR.

2. The compound of claim 1, wherein:

$R_2$ is substituted with $(Ar)_n$; and n is 1–2.

3. The compound of claim 2, wherein said compound is 4,4-diphenylcyclohexl (2S)-1-(3,3-dimethyl-2-oxopentanoyl)-pyrrolidine-2-carboxylate of formula III.

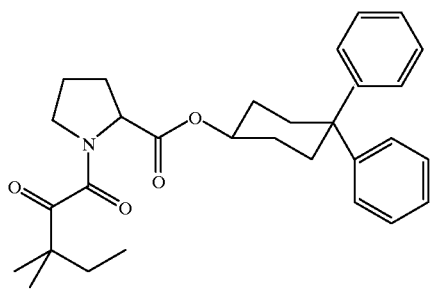

III or a pharmaceutically acceptable salt, ester, or solvate thereof.

4. The compound of claim 1, wherein $R_2$ is $C_3$–$C_9$ cycloalkyl or $C_3$–$C_9$ cycloalkenyl.

5. The compound of claim 4, wherein A and B are taken together to together to form a 5-membered ring.

6. A pharmaceutical composition comprising;

(i) an effective amount of a compound of formula II

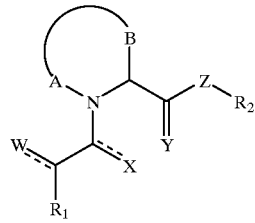

II or a pharmaceutically acceptable salt, ester, or solvate thereof, wherein:

A and B, taken together with the carbon atoms to which they are respectively attached, form a 5 membered saturated or unsaturated heterocyclic ring having one nitrogen heteroatom;

R and $R_1$ are independently $C_1$–$C_9$ straight or branched chain alkyl, $C_2$–$C_9$ straight or branched chain alkenyl, $C_3$–$C_9$ cycloalkyl, $C_3$–$C_9$ cycloalkenyl, or Ar,
wherein said R and $R_1$ are independently unsubstituted or substituted with one or more substituent (s) and the carbon atoms of said alkyl, alkenyl, cycloalkyl, and cycloalkenyl are independently unsubstituted or substituted with one or more heteroatom(s);

$R_2$ is $C_3$–$C_9$ cycloalkyl, $C_3$–$C_9$ cycloalkenyl or Ar,
wherein said cycloalkyl, cycloalkenyl, or Ar is substituted with one or more substituent(s), and the carbon atoms of said cycloalkyl and cycloalkenyl are independently unsubstituted or substituted with one or more heteroatom(s);

Ar is an aromatic or carbocyclic ring having an individual ring size of 5–9 members, or a mono-, bi- or tricyclic, heterocyclic ring having an individual ring size of 5–9 members,
said heterocyclic ring containing one or more heteroatom(s) independently selected from the group consisting of O, S, SO, $SO_2$, N, NH and NR;

W is O, S, $CH_2$ or $H_2$;

X is O or S;
Y is O or S; and
Z is O, NH or NR; and
(ii) a pharmaceutically acceptable carrier.

7. The pharmaceutical composition of claim 6, wherein:
$R_2$ is substituted with $(Ar)_n$; and
n is 1–2.

8. The pharmaceutical composition of claim 7, wherein said compound is 4,4-diphenylcyclohexl (2S)-1-(3,3-dimethyl-2-oxopentanoyl)-pyrrolidine-2-carboxylate of formula III

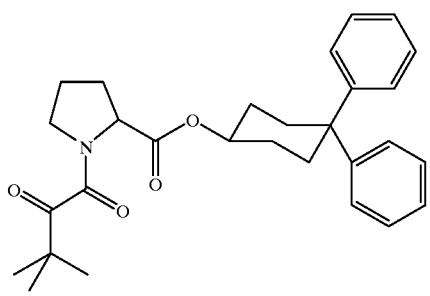

III

Or pharmaceutically acceptable salt, ester or solvate thereof.

9. The pharmaceutical composition of claim 6, wherein $R_2$ is $C_3$–$C_9$ cycloalkyl or $C_3$–$C_9$ cycloalkenyl.

10. The pharmaceutical composition of claim 9, wherein A and B are taken together to together to form a 5-membered ring.

11. A method of effecting a neuronal activity in an animal, comprising administering to said animal an effective amount of a compound of formula II

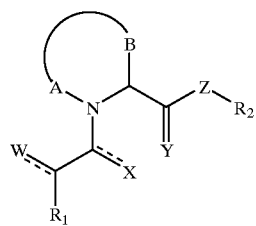

II or a pharmaceutically acceptable salt, ester, or solvate thereof, wherein:

A and B, taken together with the carbon atoms to which they are respectively attached, form a 5 membered saturated or unsaturated heterocyclic ring having one nitrogen heteroatom;

R and $R_1$ are independently $C_1$–$C_9$ straight or branched chain alkyl, $C_2$–$C_9$ straight or branched chain alkenyl, $C_3$–$C_9$ cycloalkyl, $C_3$–$C_9$ cycloalkenyl, or Ar, wherein said R and $R_1$ are independently unsubstituted or substituted with one or more substituent(s) and the carbon atoms of said alkyl, alkenyl, cycloalkyl, and cycloalkenyl are independently unsubstituted or substituted with one or more heteroatom(s);

$R_2$ is $C_{3-C9}$ cycloalkyl, $C_3$–$C_9$ cycloalkenyl or Ar, wherein said cycloalkyl, cycloalkenyl, or Ar is substituted with one or more substituent(s), and the carbon atoms of said cycloalkyl and cycloalkenyl are independently unsubstituted or substituted with one or more heteroatom(s);

Ar is an aromatic or carbocyclic ring having an individual ring size of 5–9 members, or a mono-, bi- or tricyclic, heterocyclic ring having an individual ring size of 5–9 members,
said heterocyclic ring containing one or more heteroatom(s) independently selected from the group consisting of O, S, SO, $SO_2$, N, NH and NR;

W is O, S, $CH_2$ or $H_2$;
X is O or S;
Y is O or S; and
Z is O, NH or NR.

12. The method of claim 11, wherein the neuronal activity is selected from the group consisting of stimulation of damaged neurons, promotion of neuronal regeneration, prevention of neurodegeneration and treatment of neurological disorder.

13. The method of claim 12, wherein the neurological disorder is selected from the group consisting of peripheral neuropathy caused by physical injury or disease state, traumatic injury to the brain, physical damage to the spinal cord, stroke associated with brain damage, and neurological disorder relating to neurodegeneration.

14. The method of claim 13, wherein the neurological disorder relating to neurodegeneration is selected from the group consisting of Alzheimer's Disease, Parkinson's Disease, and amyotrophic lateral sclerosis.

15. The method of claim 11, wherein said compound is immunosuppressive.

16. The method of claim 11, wherein said compound is non-immunosuppressive.

17. The method of claim 11, wherein said compound has an affinity for an FKBP-type immunophilin.

18. The method of claim 17, wherein the FKBP-type immunophilin is FKBP-12.

19. The method of claim 11, wherein:
$R_2$ is substituted with $(Ar)_n$; and
n is 1–2.

20. The method of claim 19, wherein said compound is 4,4-diphenylcyclohexl (2S)-1-(3,3-dimethyl-2-oxopentanoyl)-pyrrolidine-2-carboxylate of formula III

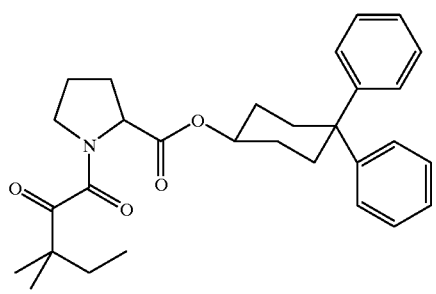

III or a pharmaceutically acceptable salt, ester, or solvate thereof.

21. The method of claim 11, wherein $R_2$ is $C_3$–$C_9$ cycloalkyl or $C_3$–$C_1$ cycloalkenyl.

22. The method of claim 21, wherein A and B are taken together to together to form a 5-membered ring.

* * * * *